United States Patent
Elgaard et al.

(10) Patent No.: US 9,687,244 B2
(45) Date of Patent: Jun. 27, 2017

(54) VASCULAR CLOSURE DEVICE

(71) Applicant: COOK MEDICAL TECHNOLOGIES LLC, Bloomington, IN (US)

(72) Inventors: Per Elgaard, Haslev (DK); Erik E. Rasmussen, Slagelse (DK); Edwin E. Macatangay, Bloomington, IN (US); Sarah E. Reeves, Cory, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 84 days.

(21) Appl. No.: 14/328,103

(22) Filed: Jul. 10, 2014

(65) Prior Publication Data

US 2015/0018857 A1    Jan. 15, 2015

(30) Foreign Application Priority Data

Jul. 10, 2013   (GB) .................................. 1312385.6

(51) Int. Cl.
| | |
|---|---|
| *A61B 17/12* | (2006.01) |
| *A61F 2/848* | (2013.01) |
| *A61F 2/91* | (2013.01) |
| *A61B 17/00* | (2006.01) |
| *A61F 2/958* | (2013.01) |

(52) U.S. Cl.
CPC .. *A61B 17/12109* (2013.01); *A61B 17/12031* (2013.01); *A61B 17/12172* (2013.01); *A61F 2/848* (2013.01); *A61F 2/91* (2013.01); *A61B 2017/00526* (2013.01); *A61B 2017/00867* (2013.01); *A61B 2017/1205* (2013.01); *A61F 2/958* (2013.01); *A61F 2002/8483* (2013.01)

(58) Field of Classification Search
CPC ........ A61B 17/12022; A61B 17/12027; A61B 17/12031; A61B 17/12036; A61B 17/1204; A61B 17/12099; A61B 17/12109; A61B 17/12113; A61B 17/12122; A61B 17/1214; A61B 17/12145; A61B 17/12168; A61B 17/12172; A61B 2017/1205; A61B 2017/12054; A61B 2017/12081
See application file for complete search history.

(56) References Cited

U.S. PATENT DOCUMENTS

| | | | |
|---|---|---|---|
| 5,709,224 | A | 1/1998 | Behl et al. |
| 6,491,707 | B2 | 12/2002 | Makower et al. |

(Continued)

FOREIGN PATENT DOCUMENTS

| | | |
|---|---|---|
| DE | 4412311 | 10/1995 |
| EP | 0781528 | 7/1997 |
| WO | WO 97/27893 | 8/1997 |

*Primary Examiner* — Todd J Scherbel
(74) *Attorney, Agent, or Firm* — Brinks Gilson & Lione

(57) ABSTRACT

A vascular closure device includes a frame to which there is fitted a plurality of anchor elements, spaced radially around the frame. The closure device includes a radial compression feature, which may be a memorized shape of the frame or non-sprung condition of the frame, having a small radius. The closure device is deployed in a vessel such that the anchor elements are embedded into the vessel wall. The radial compression feature causes the frame to compress radially, as a result of which the anchor elements will pull the vessel wall inwardly, thereby closing the vessel.

7 Claims, 2 Drawing Sheets

(56) References Cited

U.S. PATENT DOCUMENTS

| | | | |
|---|---|---|---|
| 6,527,800 B1* | 3/2003 | McGuckin, Jr. | A61B 17/12109 |
| | | | 623/1.19 |
| 6,645,205 B2* | 11/2003 | Ginn | A61B 17/0644 |
| | | | 128/200.24 |
| 2005/0055082 A1 | 3/2005 | Ben Muvhar et al. | |
| 2005/0107867 A1 | 5/2005 | Taheri | |
| 2010/0198254 A1 | 8/2010 | Schaeffer | |
| 2011/0166593 A1* | 7/2011 | Paul, Jr. | A61B 17/12022 |
| | | | 606/200 |

* cited by examiner

VASCULAR CLOSURE DEVICE

CROSS-REFERENCE TO RELATED APPLICATIONS

The present patent document is related to and claims the benefit of priority to British patent application number GB 1312385.6, filed Jul. 10, 2013, which is incorporated herein by reference in its entirety.

TECHNICAL FIELD

The present invention relates to a vascular closure device or occluder and to a method of closing or occluding a vessel.

BACKGROUND

Vascular occluders are well known for occluding bodily vessels and are produced in a variety of forms, for instance as a plug which is fitted into a patient's vessel. They may act to create substantially instantaneous occlusion of a vessel, in which case the structure of the plug provides an impermeable barrier to fluid, or they may act to occlude the vessel over time, in which case the plug will generally have a pervious membrane or structure designed to slow the flow of blood through the vessel. The membrane or structure promotes thrombosis of the blood and eventual occlusion of the vessel by the formed thrombus.

Vascular plugs are typically deployed endoluminally through the patient's vasculature up to the intended site of treatment. For this purpose, it is important to be able to compress the vascular plug radially so as to fit within an introducer assembly of a diameter which can pass readily through the patient's vessels from a remove percutaneous entry site. To this end, it is known to have vascular occluders which are able to be pulled to an elongate form, which minimizes their lateral dimensions and thus enables them to be deployed through catheters of very small diameter. While such designs of plug can optimize the delivery of the plug through the patient's vasculature, particularly where this is tortuous and/or narrow, a plug which expands from an elongate form to a shorter form cannot be positioned precisely in a patient's vessel, which can make such designs unsuitable when the treatment site is short, for example between closely located branch vessels and so on.

Vascular plugs also generally have specific operating diameters, designed to ensure occlusion as well as reliable fixation to the vessel wall so as to minimize the risk of migration of the plug over time. These plugs, however, are vessel-size specific and it is therefore necessary to determine vessel size accurately before treatment, as well as to have available for use a stock of different size plugs. Even with selection of a plug of the correct size, changes in the dimensions or shape of a vessel over time can cause imprecise occlusion and risk of migration of the plug. Vascular plugs can be prone to leakage and in some cases to recanalization. Problems tend to be greater with larger vessels.

Another method of closing or occluding a body vessel involves compressing, typically by ligation, the vessel from the outside to pinch the vessel closed, such that the vessel walls act as the barrier to blood flow. However, this method involves an open surgical procedure which is not optimal in many circumstances. Moreover, closure from the outside is not always possible, for instance in cases where the vessel is not accessible, for instance in an organ.

Known designs of vascular occluder can be found, for example, in U.S.-2005/055,082, U.S.-2005/107,867, U.S. Pat. No. 5,709,224, WO-97/027,893, U.S. Pat. No. 6,491,707, U.S.-2010/0,198,254, EP-0781528 and DE-4,412,311.

BRIEF SUMMARY

The present invention seeks to provide an improved vascular closure device or occluder and method of closing or occluding a body vessel.

According to an aspect of the present invention, there is provided a vascular closure device including: a frame of tubular form and comprising a plurality of frame elements, which frame is radially compressible to a small radius and radially expandable; a plurality of tissue grasping elements coupled to and extending radially outwardly from at least some of the frame elements; a radial compression mechanism, integral with the frame; the device being of a type detachable from an introducer assembly; the closure device being implantable in a patient, whereby the radial compression mechanism is effective to compress radially the frame within the vessel with vessel tissue grasped by and pulled by the grasping elements.

In practice, this structure of closure device can be deployed in a patient's vessel via an endoluminal introduction procedure, expanded to the vessel wall such that the tissue grasping elements attach to the vessel wall, then radially constricted by the compression mechanism so as to pull the vessel wall closed. The detachable characteristic of the device enables the closure device to be released from the introducer assembly and left in the patient.

The vascular closure device taught herein can be used in a variety of vessel sizes as the tissue grasping elements can be radially expanded to a large variety of diameters and then radially collapsed or constricted to close the vessel.

The advantage of this structure, therefore, is that vascular occlusion does not rely upon the provision of a plug, which may fail to occlude properly, be liable to recanalization or migration and so on. The closure device achieves occlusion by means of the vessel walls and yet without requiring an open surgical procedure.

In one embodiment, the frame is made of shape memory or spring material.

The tissue grasping elements may include one or more barbs. It is preferred, though, that the tissue grasping elements include one or more rearwardly extending hooks. Such a structure can ensure that the tissue grasping elements penetrate into the vessel wall and are not then removable, ensuring reliable attachment of the frame to the vessel walls and thus reliable collapse of the vessel walls to achieve occlusion of the vessel.

In a practical embodiment, the anchor elements are disposed circumferentially around said frame. This is not essential, though, as the tissue grasping elements may be disposed in opposing directions, on what could be described as opposite sides of the device, so as to close the vessel by a two-sided pulling action equivalent to a two-sided squashing effect.

Preferably, the frame has a longitudinal length and the tissue grasping elements are disposed along the length of the frame. Advantageously, the tissue grasping elements are disposed longitudinally along the length and circumferentially around the frame.

In one embodiment, the radial compression mechanism is an non-stretched or a memorized shape of the frame at said small radius. Thus, the frame can be expanded, for instance by a balloon, which will stretch the frame structure, whereupon on removal of the expansion force the frame will spring back to its radially contracted configuration. Not further or separate contraction mechanism is necessary.

The frame may have an elongate tubular form and the tissue grasping elements extend radially outwardly from the tubular form. The tubular form preferably has an operating rest condition at said small radius.

Advantageously, when at said small radius, the frame provides a small or substantially closed lumen therethrough.

It is preferred that the frame radially constricts to leave no lumen through the vessel. However, is some embodiments there may be a small lumen or opening, in which case, it is preferred that there are provided thrombogenic fibres, a gel or other barrier disposed on or in the frame, or a valve element. Advantageously, thrombogenic fibers, gel or other barrier are disposed to extend radially inwardly of the frame.

According to another aspect of the present invention, there is provided a method of closing or occluding a vessel. The method includes a first step of fitting into the vessel a vascular closure device by means of a delivery assembly, which closure device includes: a frame of tubular form and comprising a plurality of frame elements, which frame is radially compressible to a small radius and radially expandable; a plurality of tissue grasping elements coupled to and extending radially outwardly from at least some of the frame elements; a radial contraction mechanism, integral with the frame; the device being of a type detachable from an introducer assembly; the closure device being implantable in a patient.

In a second step, the method includes radially expanding the closure device in the vessel such that the tissue grasping elements embed into the vessel wall.

In a third step, the method includes allowing for radial contraction of the frame, thereby to close the vessel wall.

In a fourth step, the method includes detaching the vascular closure device from the delivery assembly, thereby to leave the vascular closure device in the vessel in the radially contracted configuration, thereby to occlude the vessel.

In one embodiment, the radial contraction mechanism of the vascular plug is an non-stretched or a memorized shape of the frame at said small radius; the method including the steps of radially expanding the frame during deployment, and removing the radial expansion thereby to allow the frame to compress radially to its small radius configuration.

Other aspects and advantages of the teachings herein will become apparent from the description of the preferred embodiments which is set out below.

BRIEF DESCRIPTION OF THE DRAWINGS

Embodiments of the present invention are described below, by way of example only, with reference to the accompanying drawings, in which.

DETAILED DESCRIPTION OF THE DRAWINGS AND THE PRESENTLY PREFERRED EMBODIMENTS

Figure 1:
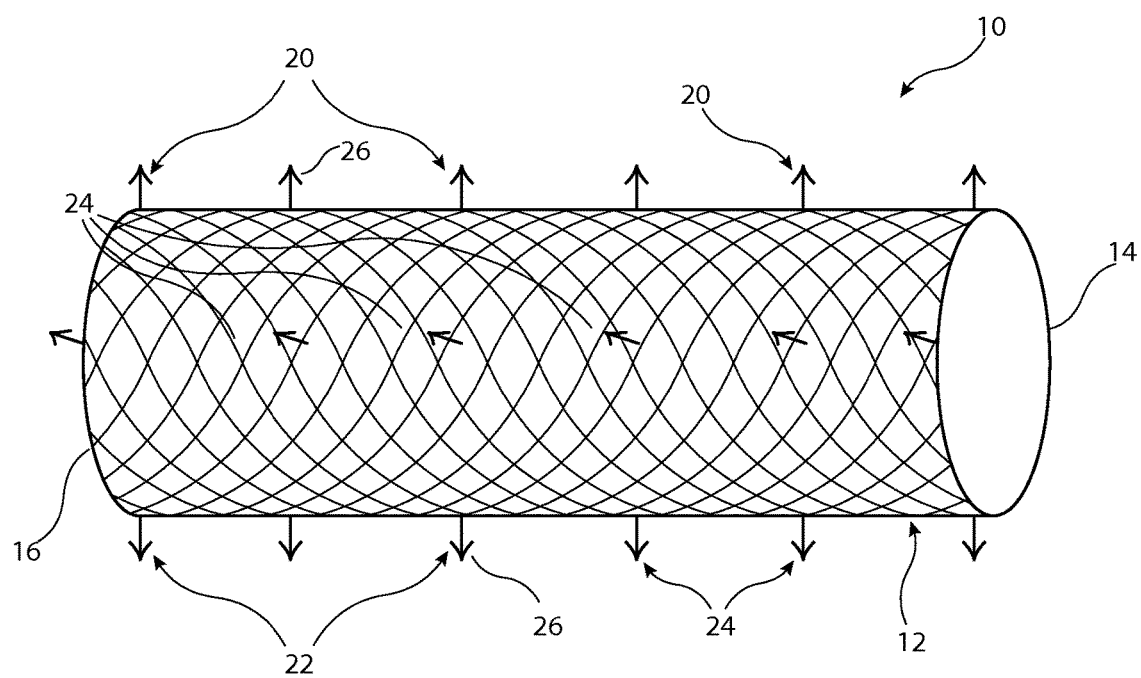
FIG. 1 is a side elevational schematic view of an embodiment of vascular closure device.

The preferred embodiments disclosed herein relate to a vascular closure device designed to deployed in a patient's vessel to occlude the vessel, arrest or prevent hemorrhaging or for devitalizing a structure or organ by occluding its blood supply. The device can be used, for example, to stop blood flow to tumors, into aneurysms, to stop blood flow to organs prior to their removal and to stop abnormal blood flow such as arteriovenous malformation (AVM) or arteriovenous fistula (AVF), for stopping bleeding and so on.

It is preferred that the device provides instantaneous closure or occlusion of a vessel, for which purpose the vascular plug is designed to stop all of or practically all of the flow of blood past the closure device substantially immediately on deployment. In other embodiments, the closure device may be designed so as to slow the flow of blood therethrough, promoting embolization and resultant occlusion of the vessel after formation of thrombi.

It is to be understood that reference to vessel closure made herein is considered a form of vascular occlusion.

The embodiments depicted in the drawings are of schematic form only, although a person skilled in the art will readily appreciate that they disclose the structural elements making up these embodiments. Even though the drawings are schematic, it is to be understood that they form an integral part of the disclosure herein, in particular having regard to the features explicitly shown and inherently part of the structures.

Referring first to FIG. 1, this shows a first embodiment of vascular closure device or occluder 10 which is in the form of a tubular stent 12, having a proximal end 14 and a distal end 16. The stent 12 may have any structure which enables it to expand and contract in the radial dimension and in one embodiment may have a structure similar to that of a conventional stent used for supporting a body lumen in an open condition, that is to have a series of sinusoidal or zigzag stent rings coupled to one another by tie bars to form a tubular structure. Other structures are also suitable, including a braided wire structure.

The stent 12 forms a frame of the device 10, the frame having a plurality of frame elements which are the stent struts, as is known in the art. In FIG. 1, the stent 12 is shown in a radially expanded condition which, as stated below, is a stretched condition of the device 10. In its normal rest configuration, the stent or frame 12 has a very small radius; that is the frame is radially contracted, such that the lumen 18 passing through the inside of the stent 12 is substantially closed or very small. In order to achieve such a rest, that is non-stretched, condition of the frame 12, this could be made of a spring material which must be stretched open to attain the configuration shown in FIG. 1, but may likewise be made of a shape memory material, such as of Nitinol, which has a very small diameter in its natural unbiased rest state. This can be achieved, for example, by cutting (e.g. laser cutting) the struts of the stent 12 from a cannula and not heat setting the shape memory material in a radially expanded condition. When produced in this manner, the memory shape of the stent 12 will be that of the original cannula from which it has been cut. As explained below, the stent can be expanded by internal pressure and then provide a return force back to its minimum diameter.

As can be seen in FIG. 1, the device 10 is provided with a plurality of sets of tissue grasping or anchor elements 20-24 which are attached to the struts and/or tie bars of the frame of the stent 12 and extend radially outwardly of the frame 12. In the embodiment shown in FIG. 1, there are four sets of anchor elements 20-24 (only three of which are visible), which are substantially uniformly spaced along the length of the frame 12 and in which each set of anchor elements occupies a given circumferential position around the frame 12. The anchor elements 20-24 shown in FIG. 1 extend substantially perpendicularly from the perimeter of the frame 12; that is in a radial direction and normal to longitudinal axis of the frame 12. It is to be understood, though, that the anchor elements 20-24 could extend at an angle to the longitudinal axis of the stent or frame 12, and may also extend at an angle to the radial direction. In other words, they could be disposed in sloping manner on the frame 12.

In FIG. 1, the anchor elements 20-24 are shown to having rearwardly extending hooks 26, there being a pair of hooks 26 on each anchor element. The skilled person will appreciate that these rearwardly extending hooks can take any of a variety of forms and in some embodiments there may be a single rearwardly extending hook 26 per anchor element. The rearwardly extending hooks are not, though, essential and may be omitted in some embodiments.

It is also to be understood that it is not necessary to have four sets of anchor elements 20-24 to the vascular closure device 10. Other embodiments may have just two sets, for instance at opposite circumferential positions and along the length of the stent or frame 12, while other embodiments may have three or more than four sets of anchor elements.

Figure 2:
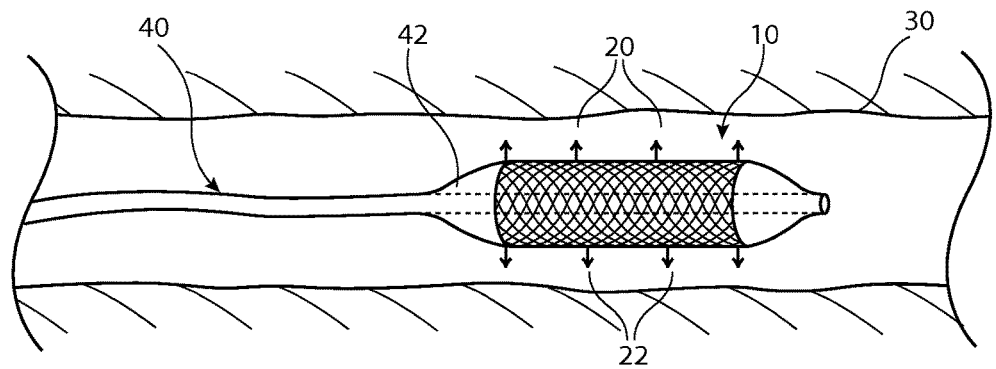
FIGS. 2 to 4 show the embodiment of vascular closure device of FIG. 1 during implantation in the vessel of a patient.
Figure 3:
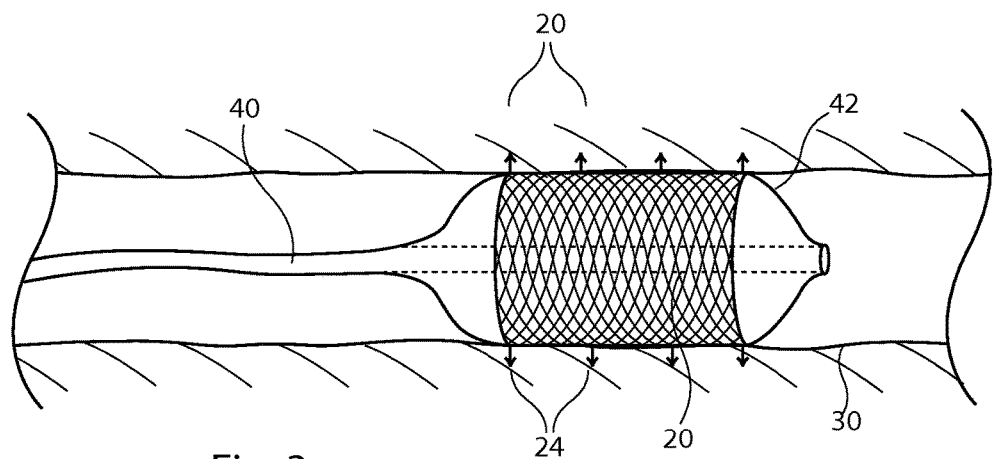
Figure 4:
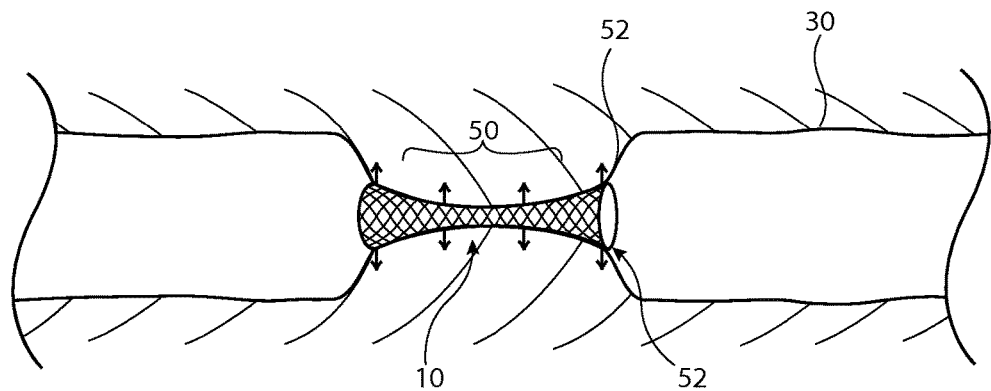

Referring now to FIGS. 2 to 4, these show the vascular closure device 10 of FIG. 1 in the process of being deployed in a patient's vessel.

FIG. 2 shows the vascular closure device 10 carried on a balloon catheter 40 of an introducer assembly (the other components of which are not shown for the sake of clarity but are commonplace). The balloon catheter 40 includes a balloon 42 which is schematically shown in a non-inflated and typically wrapped condition and over which the stent or frame 12 of the occlusion device is disposed. The skilled person will appreciate that in practice the device 10 would have a much smaller radius when fitted to a balloon catheter when the balloon 42 is non-inflated than the depiction of FIG. 2. Furthermore, as the device 10 will naturally tend to contract radially, the device need not be crimped onto the balloon as does a conventional stent, for example, and thereby will be held on the balloon by its own natural contraction force.

The vascular closure device 10 is typically introduced endoluminally through a suitable percutaneous entry point, as is well known in the art. This is typically achieved after positioning a suitable sheath or carrier catheter (not shown) up to the treatment site. Once the medical device has been located at the treatment site, the sheath or carrier catheter is pulled back to expose the medical device 10, still fitted over the balloon catheter 40. With reference to FIG. 3, the balloon 42 is then inflated so as to extend radially the stent or frame 12 of the closure device 10, which expansion causes the anchor elements 20-24 to pierce into the walls of the vessel 30. The rearwardly extending hooks 26 hook into the vessel, thereby ensuring that the anchor elements 20-24 cannot be subsequently be removed. The skilled person will appreciate that with anchor elements 20-24 suitably angled, it may not be necessary to have the rearwardly extending hooks 26.

Once the stent or frame 12 has been expanded and the anchor elements 20-24 embedded into the vessel wall, the balloon 42 can be deflated and then removed from a patient's vessel with the balloon catheter. Upon deflation of the balloon 42, the stent or frame 12 will be free to constrict to its rest diameter; that is, its unexpanded or shaped memory diameter. This can be seen in FIG. 4, the constriction of the stent or frame 12 will pull the vessel wall with it, thereby to create a constriction in the vessel, as shown by reference numeral 50 in FIG. 4, which in practice will close the vessel. The narrowing wall section 52, which closes towards the constricted section 50, provides a wall to the flow of blood.

The vascular closure device 10 will remain within the patient indefinitely, or until it is intentionally removed in a subsequent medical procedure.

It is preferred that the stent or frame 12 will constrict or collapse so as to close completely the lumen 18 and thereby provide complete and substantially immediate occlusion of the vessel. In some embodiments, though, even in its collapsed state the frame 12 may still provide a narrow lumen 18 therethrough. Such a narrow lumen may in itself provide effective occlusion of the vessel 30 by virtue of its small size. It is envisaged that the device 10 may contract to a diameter of around 1 millimeter (mm). In some such embodiments, it is envisaged that the closure device 10 may be provided with thrombogenic fibers, either at the proximal end 14 of the device 10 (such as at the upstream end) or within the frame 12, for example by being attached to or intertwined with the framework of the stent or frame 12, or a combination of the two. Thrombogenic fibers will eventually cause blood clotting and thus create a complete occlusion barrier within the vessel 30. In other embodiments, there may be provided swelling hydrogel within the lumen of the device, graft material or even one or more baffles on the internal surface of the frame 12 which act to close the lumen 18 when the frame 12 is in its radially collapsed condition. Such elements may either block blood flow or promote blood clotting or perform both actions.

The skilled person will appreciate that the contracting force produced by the device 10 will be dependent upon the vessel in which it is implanted, the strength of the vessel wall and opening pressure of blood in the vessel. In one example, the device 10 could produce a closing pressure of around 5 Newtons (N); meaning that for a device of 20 millimeters in length the closing force of the device will be in the region of 0.25 N/mm. Of course, for more delicate vessels the closing force may be less, whereas for large vessels the closing force may be greater.

The tubing from which the frame 12 is formed (for instance from which it is laser cut) may typically have a wall thickness of around 1 millimeter or so. The skilled person will appreciate that this will be dependent upon the overall dimensions of the device 10 and the constricting force which is desired the device creates.

In cases where there are provided just two sets of anchor elements 20-24, typically at opposing circumferential positions of the frame 12, these will close or pinch the vessel 30 from opposing sides so as to cause this to flatten and close in this manner.

The skilled person will appreciate that although the embodiments of FIGS. 1 to 4 show a frame 12 which is substantially cylindrical along its length, and which is substantially circular in transverse cross-section, the frame 12 may have a variety of transverse shapes and can have any shape which optimizes closure or minimization of the lumen 18 therethrough. The frame or stent 12 can be made to expand to a have a generic circular cylindrical shape by means of a balloon 42 and the resiliency of the frame structure.

It is not necessary for the frame 12 to be of uniform shape or size along its length.

The closure device 10 shown in FIG. 1 to 4 intrinsically includes a detachment characteristic for enabling it to detach from the introducer assembly such that it can be implanted indefinitely into a patient while the components of the introducer assembly are removed from the patient. The closure device 10 can therefore be a permanent implant in the patient, although it is not excluded that it could be removed by a subsequent medical procedure.

The anchor elements 20 may in some embodiments be provided with a stop element, which in the preferred embodiment is a small plate or disk fixed to the arm of the anchor element 20 and extending substantially transversely to the arm. Each stop element is spaced from its associated anchor element, typically by a few millimeters, for example 2 to 5 millimeters. In some cases this may be less and in the case for large vessels it may be larger. The stop elements are provided to prevent excessive penetration of the arms into the walls of the vessel.

It will be appreciated from the above that the closure device or occluder taught herein provides closure or occlusion by a mechanism different from the prior art, avoiding potential disadvantage of vascular occluders which act as plugs and also of pinching a vessel from the outside by way of an open surgical procedure.

It is to be understood that the above-described embodiments are examples only of the invention taught herein and that the invention could be embodied in different forms.

The disclosure in the abstract accompanying this application is incorporated herein by reference.

It will be appreciated that in some embodiments it is not necessary to have rearwardly extending hooks on the anchor elements as these may be angled with respect to the normal to longitudinal direction of the closure device and thus to the vessel, being angled in such a manner that the anchor elements will act to pull the vessel wall closed upon compression of the frame of the closure device.

The invention claimed is:

1. A method of closing or occluding a vessel, including the steps of:
    fitting into the vessel a vascular closure device by means of a delivery assembly, which closure device includes: a frame of tubular form and comprising a plurality of frame elements, the frame having an open lumen formed therethrough such that the vascular closure device can be carried on an introducer assembly, the vascular closure device not incorporating a plug member disposed therein, the frame being radially contractible to a small radius configuration and radially expandable; a plurality of tissue grasping elements coupled to and extending radially outwardly from at least some of the frame elements; a radial contraction mechanism, integral with the frame; the closure device being of a type detachable from the introducer assembly; the closure device being implantable in a patient;
    radially expanding the closure device in the vessel such that the tissue grasping elements embed into the vessel wall;
    allowing for radial contraction of the frame with the tissue grasping elements extending radially outward from the frame, thereby to close the vessel wall; and
    detaching the vascular closure device from the delivery assembly, thereby to leave the vascular closure device in the vessel in the small radius configuration, thereby to occlude the vessel.

2. The method according to claim 1, wherein the radial contraction mechanism of the vascular closure device is a non-stretched or a memorized shape of the frame at said small radius configuration; the method including the steps of radially expanding the frame during deployment, and removing the radial expansion thereby to allow the frame to compress radially to its small radius configuration.

3. The method according to claim 1, wherein the tubular frame is expanded by means of an inflatable balloon positioned inside the frame.

4. The method of claim 1, wherein after the step of allowing for radial contraction, the lumen of the vascular closure device remains open.

5. A method of closing or occluding a vessel, including the steps of:
    fitting into the vessel a vascular closure device by means of a delivery assembly, which closure device includes: a frame of tubular form and comprising a plurality of frame elements, the frame having an open lumen formed therethrough such that the vascular closure device can be carried on an introducer assembly, the frame being is radially contractible to a small radius configuration and radially expandable; a plurality of tissue grasping elements coupled to and extending radially outwardly and substantially perpendicularly from at least some of the frame elements; a radial contraction mechanism, integral with the frame; the closure device being of a type detachable from the introducer assembly; the closure device being implantable in a patient;
    radially expanding the closure device in the vessel such that the tissue grasping elements embed into the vessel wall;
    allowing for radial contraction of the frame, thereby to close the vessel wall without disposing a plug member within the vascular closure device; and
    detaching the vascular closure device from the delivery assembly, thereby to leave the vascular closure device in the vessel in the small radius configuration, thereby to occlude the vessel.

6. The method of claim 5, wherein the radial contraction mechanism of the vascular closure device is a non-stretched or a memorized shape of the frame at said small radius configuration; the method including the steps of radially expanding the frame during deployment, and removing the radial expansion thereby to allow the frame to compress radially to its small radius configuration.

7. The method of claim 5, wherein the tubular frame is expanded by means of an inflatable balloon positioned inside the frame.

* * * * *